United States Patent [19]
Yoon

[11] Patent Number: 5,788,676
[45] Date of Patent: Aug. 4, 1998

[54] ENDOSCOPIC PORTAL HAVING MULTIPLE UNIVERSAL SEALS AND METHOD OF INTRODUCING INSTRUMENTS THERETHROUGH

[76] Inventor: InBae Yoon, 2101 Highland Ridge Dr., Phoenix, Md. 21131

[21] Appl. No.: 621,499

[22] Filed: Mar. 25, 1996

[51] Int. Cl.⁶ .................................................. A61M 5/00
[52] U.S. Cl. ............................................ 604/167; 604/164
[58] Field of Search ................................ 604/164, 167, 604/256, 195, 174

[56] References Cited

U.S. PATENT DOCUMENTS

| | | |
|---|---|---|
| 1,986,484 | 11/1932 | Schlueter . |
| 3,565,078 | 2/1971 | Vailliancourt . |
| 3,585,996 | 6/1971 | Reynolds . |
| 3,620,500 | 11/1971 | Santomieri . |
| 3,994,287 | 11/1976 | Turp et al. . |
| 4,177,814 | 12/1979 | Knepshield et al. . |
| 4,180,068 | 12/1979 | Jacobsen et al. . |
| 4,240,411 | 12/1980 | Hosono . |
| 4,243,034 | 1/1981 | Brandt . |
| 4,475,548 | 10/1984 | Muto . |
| 4,535,773 | 8/1985 | Yoon . |
| 4,654,030 | 3/1987 | Moll et al. . |
| 4,673,393 | 6/1987 | Suzuki et al. ............................ 604/167 |
| 4,705,511 | 11/1987 | Kocak ..................................... 604/167 |
| 4,842,591 | 6/1989 | Luther . |
| 4,874,378 | 10/1989 | Hillstead . |
| 4,895,346 | 1/1990 | Steigerwald ......................... 604/167 X |
| 4,899,729 | 2/1990 | Gill et al. . |
| 4,917,668 | 4/1990 | Haindl . |
| 4,929,235 | 5/1990 | Merry et al. . |
| 4,966,587 | 10/1990 | Baumgart ............................ 604/167 X |
| 4,978,341 | 12/1990 | Niederhauser . |
| 4,994,027 | 2/1991 | Deem et al. . |
| 5,108,380 | 4/1992 | Herlitze et al. . |
| 5,127,626 | 7/1992 | Hilal et al. . |
| 5,141,498 | 8/1992 | Christian . |
| 5,158,553 | 10/1992 | Berry et al. . |
| 5,161,773 | 11/1992 | Tower . |
| 5,167,636 | 12/1992 | Clement . |
| 5,176,651 | 1/1993 | Allgood et al. ........................ 604/167 |
| 5,176,659 | 1/1993 | Mancini . |
| 5,180,373 | 1/1993 | Green et al. . |
| 5,188,607 | 2/1993 | Wu . |
| 5,197,955 | 3/1993 | Stephens et al. . |
| 5,201,714 | 4/1993 | Gentelia et al. . |
| 5,207,656 | 5/1993 | Kranys . |
| 5,226,879 | 7/1993 | Ensminger et al. ................. 604/167 X |
| 5,269,763 | 12/1993 | Boehmer et al. . |
| 5,282,790 | 2/1994 | Clement . |
| 5,300,035 | 4/1994 | Clement . |
| 5,308,336 | 5/1994 | Hart et al. . |
| 5,324,270 | 6/1994 | Kayan et al. . |
| 5,350,364 | 9/1994 | Stephens et al. . |
| 5,360,417 | 11/1994 | Gravener et al. . |
| 5,382,553 | 1/1995 | Hart et al. . |
| 5,389,080 | 2/1995 | Yoon . |
| 5,391,153 | 2/1995 | Haber et al. . |
| 5,391,154 | 2/1995 | Young ..................................... 604/167 |
| 5,429,609 | 7/1995 | Yoon . |
| 5,441,486 | 8/1995 | Yoon . |
| 5,460,616 | 10/1995 | Weinstein . |
| 5,476,475 | 12/1995 | Gadberry . |
| 5,496,280 | 3/1996 | Vandenbroek et al. . |

*Primary Examiner*—Sam Rimell

[57] ABSTRACT

An endoscopic portal for establishing communication with a body cavity for the introduction of instruments through the endoscopic portal includes a first seal having a variable size passage to permit instruments of varying sizes to passed therethrough, a second seal disposed distally of the first seal and having a variable size passage axially aligned with the variable size passage of the first seal, and a first tubular expander aligned with the variable size passages. The first and second seals are biased to contracted or closed positions where their variable size passages have a first cross-sectional size and are movable to expanded or open positions where the variable size passages have a second cross-sectional size larger than the first cross-sectional size. The tubular expander can be disposed between the first and second seals so that opposite axial ends of the tubular expander are insertable in the seals to move the seals from the closed position to the open position such that instruments of various sizes can be introduced through the tubular expander and the seals. Alternatively, a separate tubular expander can be provided for each seal and made to move relative to that seal in order to cause the seal to move from the closed position to the open position.

20 Claims, 3 Drawing Sheets

ENDOSCOPIC PORTAL HAVING MULTIPLE UNIVERSAL SEALS AND METHOD OF INTRODUCING INSTRUMENTS THERETHROUGH

BACKGROUND OF THE INVENTION

1. Field of the Invention

The present invention pertains to endoscopic portals for establishing communication with an internal site in a body and, more particularly, to endoscopic portals having multiple universal seals forming a seal with instruments of various sizes introduced through the endoscopic portals and to methods for introducing instruments through such universal seals.

2. Discussion of the Prior Art

In endoscopic procedures, a portal, such as a sleeve or cannula or other structure forming a passage, is normally disposed in a cavity wall such that a distal end of the portal is positioned within the cavity and a proximal end of the portal is disposed externally of the cavity to provide a passage establishing communication with an internal site from externally of the cavity. Typically, various instruments are introduced at the operative site through the passage defined by the portal in order to perform diagnostic and/or surgical procedures, with the instruments many times having varying sizes in cross-section. In endoscopic procedures, it is important to prevent undesired fluid flow to and from the internal site; and, accordingly, the portal must be sealed prior to and subsequent to the introduction of instruments and while the instruments are in place. In particular, fluid such as gaseous phase carbon dioxide or nitrous oxide are normally introduced in the body for insufflation as part of the endoscopic procedure, and the escape of such gases through the portal should be prevented.

Many endoscopic portals have valves including a valve passage having a fixed size. Instruments larger in size than the fixed size of the valve passage cannot be inserted through the valve passage into the portal; and, when instruments smaller in size then the fixed size of the valve passage are inserted, fluid can escape past the smaller size instruments. Universal seals having variable size passages for receiving and sealing engaging instruments of various sizes have been proposed for endoscopic portals. Many of the universal seals proposed for endoscopic portals are made of elastic tearable materials, and instruments inserted through the variable size passages come in contact with the tearable materials. Accordingly, there is a risk that the seals may be torn or punctured when instruments are inserted or withdrawn, particularly where the instruments inserted are sharp. In order to avoid tearing by the inserted instruments, more rigid protectors have been disposed within the seal; however, such seals, even with protectors, still have the disadvantages of being opened by contact with an instrument to be introduced and, thus, creating an obstruction to introduction of the instrument and the opportunity for tearing of the seal causing undesirable leakage of gas. Additionally, prior art universal seals increase resistance to introduction and withdrawal of instruments due to contact of the instruments with the seal and can adversely affect the instrument being inserted by such contact.

SUMMARY OF THE INVENTION

Accordingly, it is primary object of the present invention to overcome the aforementioned disadvantages of prior art endoscopic portals by permitting introduction and withdrawal of instruments without contacting a seal or valve.

Another object of the present invention is to alternatingly open each of a pair of universal seals of an endoscopic portal with a tubular expander while maintaining the other universal seal in a closed or sealed position such that an instrument can be introduced and/or withdrawn through the portal with a minimum of leakage and without contacting either of the seals.

An additional object of the present invention is to utilize opposite axial ends of a single tubular expander to open one or both of a pair of universal seals in an endoscopic portal.

A further object of the present invention is to utilize separate tubular expanders to open one or both of a pair of universal seals in an endoscopic portal.

Yet another object of the present invention is to automatically close one of a pair of universal seals in an endoscopic portal when the other universal seal is opened with a blunt expander.

Some of the advantages of the present invention over the prior art are that the universal seals can be utilized in place of conventional trocar or portal valves or in combination with conventional trocar or portal valves, that instruments inserted through the universal seals do not present a significant risk of damage to the universal seals since no contact is made by the introduced instruments with the universal seals during insertion, that the universal seals can be opened to permit introduction or withdrawal of an instrument without contact adverse to either the instrument or devices or tissue carried by the instrument, that opening of the universal seal is easily accomplished, that the need for separate protectors and universal seals is eliminated, and that the endoscopic portals according to the present invention can be reusable or disposable for single patient use since exposure to body fluids and tissue is minimized.

These and other objects, advantages and benefits are realized with the present invention as characterized in an endoscopic portal including a first seal having a variable size passage to permit instruments of varying sizes to be passed therethrough, a second seal disposed distally of the first seal and having a variable size passage axially aligned with the variable size passage of the first seal, and a first tubular expander aligned with the variable size passages. The first tubular expander is insertable in at least one of the seals to move the seal from a closed position where the variable size passage of the seal is closed to an open position where the variable size passage of the seal is opened to permit instruments of various sizes to be introduced through the tubular expander and the seal. The first tubular expander is withdrawable from the seal such that the seal is biased toward the closed position to contact instruments of various sizes in the passage to form a seal therewith. The first tubular expander can be disposed between the first and second seals and be moved relative to the seals or held stationary with the seals being moved relative to the expander, or the first tubular expander can be disposed adjacent one of the seals and a second tubular expander disposed adjacent the other seal with either the expanders or the seals being movable in order to cause the expanders to be inserted into the seals.

Another aspect of the present invention is generally characterized in a method of introducing an instrument in a body cavity using a sleeve having a distal end, a proximal end and a lumen between the distal and proximal ends, a first seal having a variable size passage, a second seal disposed distally of the first seal and having a variable size passage axially aligned with the variable size passage of the first seal, and a tubular expander longitudinally aligned with the variable size passages and being insertable in at least one of the seals. The method includes the steps of introducing the distal end of the sleeve in a body cavity, moving the tubular expander into the variable size passage of the first seal to enlarge the variable size passage to receive an instrument, introducing the instrument through the tubular expander such that the instrument extends through the first seal, withdrawing the tubular expander from the variable size passage of the first seal to allow the first seal to resiliently engage the instrument and form a seal therewith, moving the tubular expander into the variable size passage of the second seal to enlarge the variable size passage to receive the instrument, advancing the instrument distally through the tubular expander such that the instrument extends through the second seal, and withdrawing the tubular expander from the variable size passage of the second seal such that the second seal resiliently engages the instrument and forms a seal therewith. In one embodiment, the step of moving the tubular expander into the variable size passage of the first seal includes moving a first tubular expander relative to the first seal, and the step of moving the tubular expander into the variable size passage of the second seal includes moving a second tubular expander relative to the second seal. In another embodiment, the step of moving the tubular expander into the variable size passage of the first seal includes moving the tubular expander proximally from a rest position disposed between the first and second seals and the step of moving the tubular expander into the variable size passage of the second seal includes moving the tubular expander distally relative to the second seal from the rest position.

Other objects and advantages of the present invention will become apparent from the following description of the preferred embodiments taken in conjunction with the accompanying drawings wherein like parts in each of the several figures are identified by the same reference numerals or by reference numerals having the same last two digits.

DESCRIPTION OF THE PREFERRED EMBODIMENT

Figure 1:
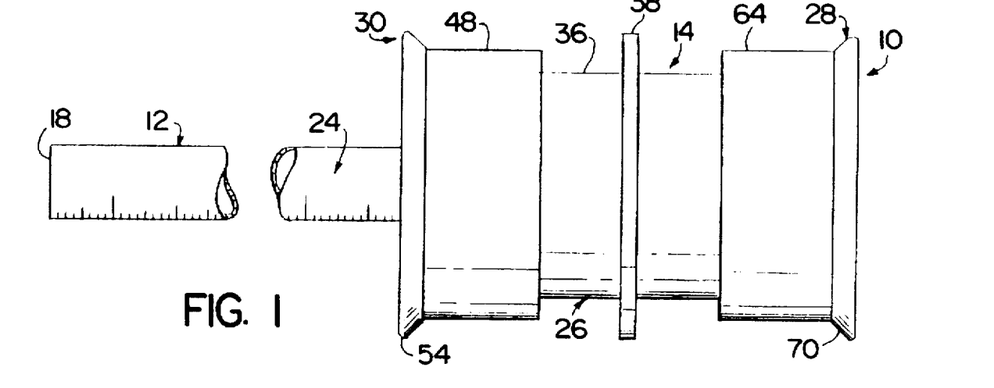
FIG. 1 is a broken side view, in elevation, of an endoscopic portal according to the present invention.
Figure 2:
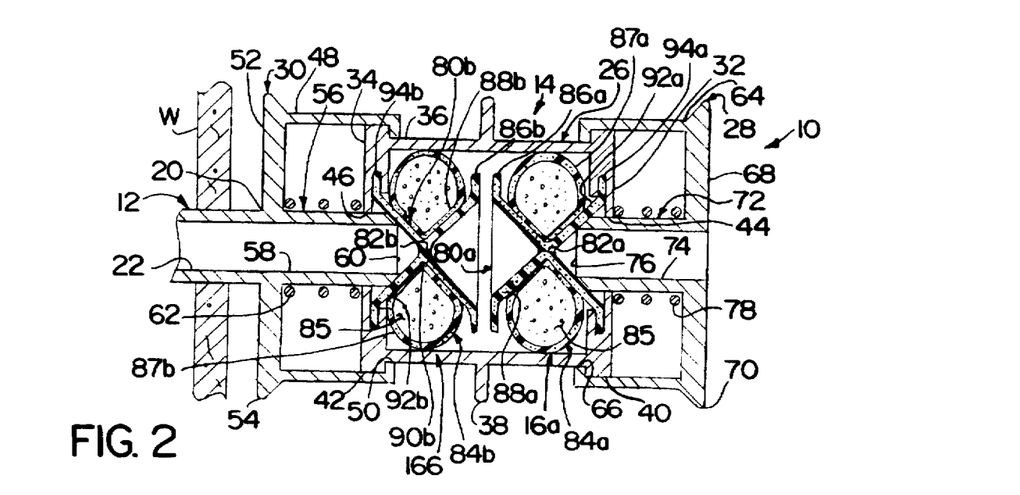
FIG. 2 is a sectional side view of the endoscopic portal of FIG. 1 showing the universal seals thereof in closed positions.

An endoscopic portal 10 according to the present invention, as illustrated in FIGS. 1 and 2, includes an elongate tubular member or sleeve 12, a housing 14 mounting a proximal end of the tubular member and a pair of universal seals 16a and 16b disposed in the housing. Tubular member 12, which, for example can take the form of a cannula or portal sleeve or a flexible structure, such as an inflatable membrane, has an open distal end 18 for being disposed at an internal site in a body cavity, an open proximal end 20 for being disposed externally of the cavity and a lumen 22 communicating between the proximal and distal ends. Proximal end 20 is coupled with housing 14 and can be integrally, unitarily formed with the housing if desired. It will be appreciated, however, that the tubular member can be made separate from the housing and coupled with or attached to the housing in various ways. For example, when the tubular member is made separately from the housing, the tubular member can be permanently attached to the housing or removably coupled with the housing such as by use of a threaded connection. Tubular member 12 can be made of any suitable rigid, semi-rigid, flexible or bendable medical grade materials such as metals or plastics as well as flexible, expandable, elastic or stretchable materials such as rubber. Lumen 22 of the tubular member has a cross-sectional size to receive instruments of various cross-sectional sizes. Where the tubular member is made of a rigid material, the lumen can have a fixed cross-sectional size to receive instruments of various cross-sectional sizes smaller than the cross-sectional size of the lumen, or the lumen can have a variable cross-sectional size. For example, a longitudinal slit can be provided in the wall of the tubular member extending the entire length thereof to permit diametric or cross-sectional expansion of the tubular member as disclosed in applicant's U.S. Pat. No. 5,429,609, the disclosure of which is incorporated herein by reference. Where the tubular member is made of stretchable material, the cross-sectional size of the lumen can be variable, with or without a longitudinal slit, due to stretching of the tubular member when instruments having cross-sectional sizes larger than the cross-sectional size of the lumen are inserted therein. A scale 24 including a plurality of indicia lines is provided along an outer or external surface of tubular member 12. The indicia lines are located at predetermined or defined distances from the distal end of the tubular member and from one another allowing the scale to be utilized to take measurements in the body. Various numerical indica can be provided on the outer surface of the tubular member to identify the distances indicated by the indica lines.

Housing 14 can be made of any suitable material, such as plastic, and can have various configurations including a cylindrical configuration as illustrated in FIG. 1. Housing 14 includes a cylindrical main body 26 and a pair of endcaps 28 and 30 slidably mounted on proximal and distal ends of the main body, respectively. Main body 26 includes proximal and distal walls 32 and 34 oriented substantially perpendicular to a longitudinal axis of the main body and a hollow, cylindrical side wall 36 extending longitudinally between the proximal and distal walls. Cylindrical side wall 36 carries or is formed with an outwardly protruding finger rest 38 of annular configuration disposed between the proximal and distal walls and oriented perpendicular to the longitudinal axis of the main body. Proximal and distal walls 32 and 34 extend radially beyond cylindrical side wall 36 to define outwardly protruding transverse flanges 40 and 42, respectively, at opposite ends of the main body. Proximal and distal walls 32 and 34 are formed with openings 44 and 46 of circular configuration which are axially or longitudinally aligned with the lumen of tubular member 12.

Flange 42 defined by distal wall 34 is disposed in an open rearward end of distal endcap 30. Endcap 30 includes a hollow, cylindrical side wall 48 configured to telescopically receive flange 42, the cylindrical side wall terminating proximally at an inwardly protruding transverse flange 50 and distally at a forward wall 52 oriented perpendicular to the longitudinal axis of the main body. Forward wall 52 extends radially beyond cylindrical side wall 48 to define an enlarged or flared circumferential forward rim 54. Endcap 30 is slidably mounted on a distal end of main body 26 with flange 42 of the main body being retained within the endcap by flange 50 of the endcap. A first tubular or hollow expander 56 extends proximally from an opening in forward wall 52 of the distal endcap and has a lumen 58 aligned with opening 46 in distal wall 34 of the main body and lumen 22 of the tubular member 12. Expander 56 terminates proximally at a proximal end 60 having a chamfered or angled peripheral edge providing a blunt configuration. A bias member 62 is shown as a coil spring disposed concentrically around expander 56 and is mounted in compression between distal wall 34 of the main body and forward wall 52 of the distal endcap to bias the distal endcap distally relative to the main body such that the endcap is normally disposed in a non-compressed condition, position or state with flange 50 in abutment with flange 42. Distal endcap 30 is slidable longitudinally along main body 26 against the bias of spring 62 to move expander 56 proximally to a compressed condition, position or state relative to the main body as will be explained further below.

Flange 40 defined by proximal wall 32 of the main body is disposed in an open forward end of proximal endcap 28. Endcap 28 includes a hollow, cylindrical side wall 64 configured to telescopically receive flange 40, and the proximal endcap terminates distally at an inwardly protruding transverse flange 66 and proximally at a rearward wall 68. Rearward wall 68 extends radially beyond cylindrical side wall 64 to define an enlarged or flared circumferential rearward rim 70. Proximal endcap 28 is slidably mounted on a proximal end of main body 26 with flange 40 of the main body being retained with the proximal end cap by flange 66 of the endcap. A second tubular or hollow expander 72 extends distally from an opening in rearward wall 68 of the endcap and has a lumen 74 aligned with opening 44 in proximal wall 32 of the main body and lumen 22 of the tubular member. Expander 72 terminates distally at a distal end 76 having a chamfered or angled peripheral edge providing a blunt configuration. A bias member 78 is shown as a coil spring disposed concentrically around the expander and is mounted in compression between the rearward wall of the proximal endcap and the proximal wall of the main body to bias the endcap proximally relative to the main body such that the endcap is normally disposed in a non-compressed condition, position or state with flange 66 in abutment with flange 40. Proximal endcap 28 is slidable longitudinally along main body 26 against the bias of spring 78 to move expander 72 distally to a compressed condition, position or state relative to the main body as will be explained further below.

The lumen of each expander preferably has a cross-sectional size at least as large as the cross-sectional size of the lumen of tubular member 12 to receive instruments of various cross-sectional sizes. The expanders can be formed integrally with the endcaps in a unitary manner, or the expanders can be formed separately of the endcaps and attached in any suitable way, such as by use of a threaded coupling or adhesive bonding. While bias members 62 and 78 are shown as coil springs disposed concentrically around the expanders, it will be appreciated that the bias members can include various types of springs or other bias devices including, but not limited to, compression springs, tension springs, pan springs, leaf springs, rubber, or magnets.

Figure 3:
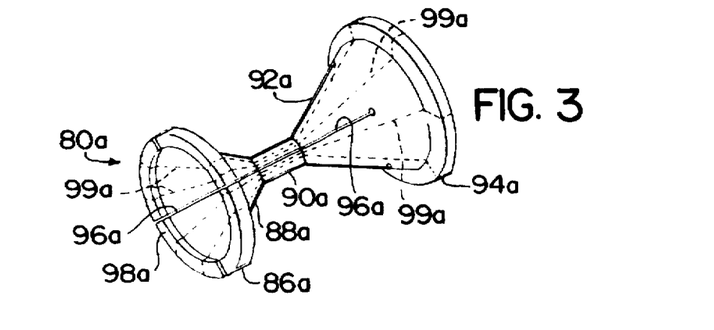
FIG. 3 is a perspective view of a seal member of a universal seal in the closed position.

Universal seals 16a and 16b are disposed in main body 26 in axially spaced relation to one another. The seals are identical in configuration but are reversed in axial orientation so that only one of the universal seals, i.e., proximal universal seal 16a, will be shown and described herein in detail, it being understood that the other universal seal, i.e., distal universal seal 16b, has identical features in reverse orientation which are referred to using the same reference numerals followed by a different letter. Proximal seal 16a includes a seal member 80a defining a variable size passage 82a and a compressible member 84a disposed around the seal member. As best seen in FIG. 3, seal member 80a includes an outwardly protruding, transverse forward or distal flange 86a, a hollow conical forward section 88a joined to the forward flange and decreasing in cross-sectional size in a proximal direction, an intermediate section 90a having an external cylindrical configuration proximally joined to the forward section, a hollow conical rearward section 92a proximally joined to the intermediate section and increasing in cross-sectional size in the proximal direction and an outwardly protruding, transverse, rearward or proximal flange 94a at a proximal end of the rearward section. A plurality of slits 96a are formed in the seal member extending longitudinally from a distal end of the seal member to terminate proximally at slit ends disposed distally or forwardly of rearward flange 94a. Seal member 80a is arranged in main body section 26 with rearward flange 94a thereof fixedly received in a recess in proximal wall 32 of the main body and with the variable size passage 82a longitudinally aligned with or in communication with the lumen of tubular member 12 and the lumen of expander 72.

Distal universal seal 16b is a mirror image of proximal seal 16a and includes a seal member 80b defining a variable size passage 82b with a compressible member 84b disposed around the seal member. Seal member 80b includes an outwardly protruding, transverse, rearward or proximal flange 86b, a hollow, conical, rearward section 88b joined to rearward flange 86b and decreasing in cross-sectional size in a distal direction, an intermediate section 90b having an external cylindrical configuration distally joined to rearward section 88b, a hollow conical forward section 92b distally joined to intermediate section 90b and increasing in cross-sectional size in the distal direction and an outwardly protruding transverse forward or distal flange 94b at a distal end of forward section 92b. A plurality of slits (not shown) are formed in seal member 80b extending longitudinally from a proximal end of the seal member to terminate distally at slit ends disposed proximally or rearwardly of forward flange 94b. Seal member 80b is arranged in main body section 26 with forward flange 94b thereof fixedly received in a recess in distal wall 34 of the main body and with the variable size passage longitudinally aligned with or in communication with the lumen of tubular member 12 and the lumen of expander 56. Accordingly, tubular member 12, expanders 56 and 72 and seal members 80a and 80b are coaxially aligned.

Preferably, three or four longitudinal slits are formed in the seal members; and, in the case of the proximal seal member shown in FIG. 3, four slits are formed through the wall of the seal member at 90° spaced locations about a longitudinal axis of the seal member to define four flexible, bendable or resilient legs 98a. The seal members are maintained in or biased to a closed, initial or contracted position by a spine 99a including a plurality of individual spring wires or stiffeners attached to the seal members. The spring wires can be disposed on the surface of the seal members or within the material forming the seal members. In the case of the seal member shown, the spring wires are disposed within the material of the seal member and oriented longitudinally along the entire length thereof to establish and/or maintain the configuration of the seal member in the closed position. In the closed position, as shown in FIGS. 2 and 3, legs 98a are biased inwardly toward one another, i.e., in the direction of the longitudinal axis of the seal members, such that slits 96a are closed or substantially closed. Longitudinal side edges of legs 98a are close to or in contact with one another such that there are little or no gaps or spaces between the legs. Inner surfaces or edges of legs 98a contact one another along the intermediate section of the seal member such that the variable size passage of the seal member is completely closed when the seal member is in the closed position prior to receiving an instrument. Since the variable size passages of the seal members are completely closed in the closed position, the seals can be utilized in place of conventional trocar or portal valves to prevent fluid flow through endoscopic portal 10. It will be appreciated, however, that the variable size passages of the seal members do not have to be completely closed in the closed or initial position and that the seals can be utilized with conventional trocar or portal valves, such as flapper and trumpet valves, integrally in housing 14 or as components attachable to housing 14.

Each of the seal members is movable to an open, expanded or stretched position wherein the legs are moved outwardly away from one another, i.e., in a direction transverse to the seal member longitudinal axis, to be spread apart from one another such that the variable size passage is open. The legs are spreadable apart a variable extent or distance such that the passage can be of variable cross-sectional size.

The seal members are preferably made of an expandable, stretchable or elastic medical grade material such as Tecoflex manufactured by Thermedics, Inc., Teflon, Gortex or Silicone and latex rubbers. However, the seal members can be made of various other materials including, but not limited to, shape memory materials and various spring materials such as stainless steel and titanium. It is desirable for the seal members to be made of a tear-resistant, slippery material. Where the seal members are made of a stretchable, elastic material, no longitudinal slits are necessary as explained hereinbelow. Where no slits are provided in the seal members, a compressible member may not be needed as explained further below. By providing a slitted seal member with an elastic or stretchable inner member, a compressible member may not be necessary as also explained below. The spring wires can be made of suitable spring material such as stainless steel or titanium. However, depending on the materials utilized for the seal members, a separate spine or stiffener may not be needed.

Compressible members 84a and 84b each include a body of compressible material 85 disposed around a respective seal member and confined by the main body of housing 14. Each compressible member includes a bladder, bag, balloon or membrane 87a or 87b made of any suitable expandable, stretchable, elastic, resilient or flexible material forming an envelope for holding compressible material 85 in the interior thereof. It is desirable that membranes 87a and 87b be made of a strong, tear-resistant material. Exemplary materials suitable for such membranes include Tecoflex, Teflon, Gortex and rubber. Each membrane has a toroidal or donut-shaped configuration with a central longitudinal passage entirely therethrough. Seal members 80a and 80b are disposed in respective passages of membranes 87a and 87b with forward flange 86a of seal member 80a attached to a distal or forward end of membrane 87a and rearward flange 86b of seal member 80b attached to a proximal or rearward end of membrane 87b. The seal members can be attached to the membranes in many various ways including adhesively as in the case of the universal seals shown. It should be appreciated that the compressible members can be attached to various parts of the seal members; however, the compressible members do not have to be attached to a seal member. Rather, the compressible members can be attached to the housing instead of the seal members or can be unattached and merely confined by the seal member and/or the housing. Compressible material 85 can be a compressible fluid or a compressible solid material including gases and liquids for exerting a compressive force or pressure on the seal members. Some suitable compressible materials include air, $CO_2$, nitrous oxide, water, saline, high density liquids such as ADG and Dextran, gel, foam or sponge. A membrane can have various predetermined sizes and configurations to cover any gaps or spaces between the legs of the seal members and/or to grip the seal members. Exemplary compressible members are disclosed in applicant's U.S. Pat. Nos. 5,389,080 and 5,429,609 which are incorporated herein by reference. The compressible members can be provided with one or more ports for supplying compressible material to the membranes and/or for removing compressible material from the compressible members such that the compressible members are adjustable in size and sealing force.

It will be appreciated that where the seal members are biased to the closed position, the compressible members need not exert a positive compressive or sealing force against the seal members prior to introduction of an instrument through the variable size passages. However, where a positive compressive or sealing force is exerted by the compressible members against the seal members in the closed position, redundant protection is provided for an enhanced seal. It will also be appreciated that the seal members do not have to be biased in the closed or initial position and that the compressible members can be designed to exert a positive pressure or force on the seal members sufficient to maintain the seal members in the closed position. Where the variable size passage of each seal member is not normally completely closed, due to the seal member not being biased or being insufficiently biased, the respective compressible member and a force exerted thereby can be utilized to completely close the variable size passage prior to receiving an instrument through the passage. However, as previously mentioned, the variable size passage does not have to be completely closed in the initial position. It should also be appreciated that the compressible member itself can serve as the seal member with the passage of the compressible member forming the variable size passage. The compressible member can be in the nature of an adjustable, fluid filled balloon to and from which fluid can be supplied; and, since the compressible member is opened by the expander, instruments do not contact the balloon during insertion and/or withdrawal of the instruments.

Further details of such universal seals are set forth in my co-pending patent application Ser. No. 08/618,328, filed on Mar. 19, 1996 entitled "Endoscopic Portal Having Universal Seals And Methods For Introducing Instruments Therethrough," the disclosure of which is incorporated herein by reference, and several embodiments of suitable universal seals are disclosed therein.

To use endoscopic portal 10, distal end 18 of tubular member 12 is disposed at an internal site in the body, and the proximal end 20 of tubular member 12 is disposed externally of the body such that tubular member 12 provides a passage or portal establishing communication with the internal site from externally of the body. Tubular member 12 is typically positioned to extend through an anatomical wall W with the use of a penetrating member, such as a trocar or needle, passing through the lumen of tubular member 12 via seals 16a and 16b. Introduction of the penetrating member through the seals is accomplished in the same manner as described hereinafter for introduction of various size instruments through the endoscopic portal. The penetrating member is utilized to penetrate the anatomical wall allowing tubular member 12 to follow the penetrating member through the wall. Once tubular member 12 has been positioned to extend through the anatomical wall, the penetrating member is withdrawn from the endoscopic portal leaving the tubular member in place. Withdrawal of the penetrating member from endoscopic portal 10 causes both seal members to automatically return to the closed position shown in FIG. 2. With seal members 80a and 80b disposed in the closed position, inner surfaces of the seal members along intermediate sections 90a and 90b, respectively, are in contact with one another such that the variable size passages are completely closed. Housing 14 will be in a noncompressed or rested state or condition with spring 78 biasing endcap 28 proximally from main body section 26 and spring 62 biasing endcap 30 distally from the main body section. With endcap 28 biased from main body section 26, distal end 76 of expander 72 will be withdrawn from or disposed proximally of intermediate section 90a of seal member 80a such that the variable size passage 82a along the intermediate section remains closed. Similarly, with endcap 30 biased from main body section 26, the proximal end 60 of expander 56 will be withdrawn from or disposed distally of intermediate section 90b of seal member 80b such that the variable size passage along the intermediate section remains closed.

Figure 4:
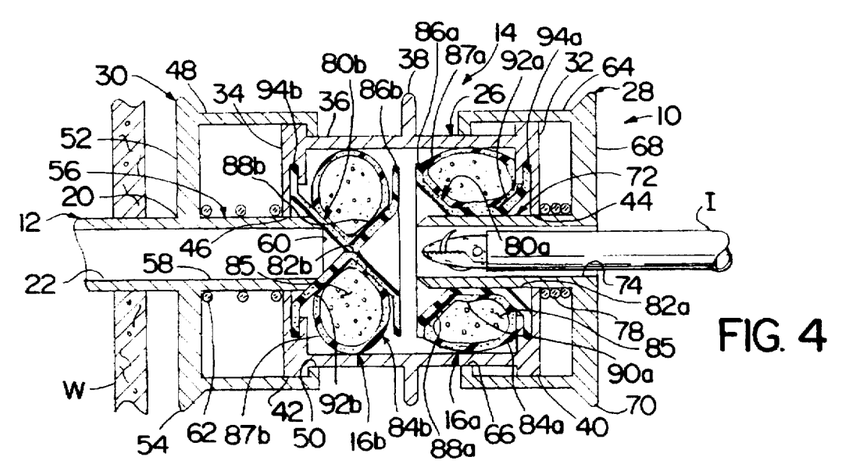
FIG. 4 is a sectional side view of the endoscopic portal of FIG. 1 showing the first, proximal universal seal in an open position.

When it is desired to introduce an instrument at the internal site through endoscopic portal 10, endcap 28 is moved longitudinally, distally relative to main body 26 against the bias of spring 78, for example by positioning a thumb on endcap 28 and one or more fingers on the distal side of finger rest 38 and then squeezing or compressing the housing to move the endcap towards the finger rest. Endcap 28 will then be in a compressed state or condition as shown in FIG. 4, and expander 72 will be moved longitudinally, distally into variable size passage 82a. Expander 72 overcomes the closing force or bias of seal member 80a and the compressive force of compressible member 84a to spread the legs of the sealing member apart from one another as facilitated by the angled peripheral edge of the expander in contact with the inner surface of the seal member. The legs are moved outwardly by the expander in a direction transverse or radial to a longitudinal axis of endoscopic portal 10 causing seal member 88 to be moved from the closed position wherein the variable size passage has a first cross-sectional size to an open position wherein the variable size passage has a second cross-sectional size larger than the first cross-sectional size. Once the distal end of expander 72 has entered forward section 88a of seal member 80a, the seal member will be in a fully opened position as shown in FIG. 4 with side edges of the legs being spaced further apart from one another and the seal member being biased toward the closed position such that inner surfaces of the seal member are in contact with the outer surface of the expander along intermediate section 90a. Movement of seal member 80a to the opened positioned compresses compressible member 84a which exerts an increased compressive force against the seal member since the compressible seal member is confined by the seal member and the housing. Therefore, seal 16a forms a seal with expander 72 due to the closing force or bias of the seal member and the compressive force of the compressible member, which fills the gaps or spaces between legs. Since the seal is opened by a blunt expander, tearing, puncturing and other damage to components of the seal is avoided. The lumen of expander 72 provides a passage through the seal member such that instruments having various cross-sectional sizes larger than the first cross-sectional size of the passage can be inserted without coming into contact with the seal and without resistance to insertion which would otherwise be presented by the seal. With seal 16a maintained in the open position, an instrument I having a cross-sectional size the same as or smaller than the cross-sectional size of the lumen of expander 72 is inserted through the lumen of the expander and into the space between seals 16a and 16b. Endcap 28 is then released allowing the endcap to automatically return to the non-compressed state with expander 72 being withdrawn proximally from the variable size passage. Once endcap 28 has returned to the non-compressed state, universal seal 16a will be in a sealing position with seal member 80a urged toward the closed position by spine 99a as well as by compressible member 84a exerting a compressive sealing force or pressure on the seal member. The compressible member occupies or fills the gaps or spaces between legs of the seal member and seal only contacts the outer surface of instrument I between the legs to complete the seal entirely along the circumference or periphery of the instrument. Accordingly, universal seal 16a engages the instrument I to form a seal therewith while allowing the instrument to be moved longitudinally through the variable size passage. It will also be appreciated that while universal seal 16a is being opened to permit introduction of the instrument I distal seal 16b remains in the closed position to prevent leakage through the endoscopic portal which might occur if only one seal or valve were provided.

Figure 5:
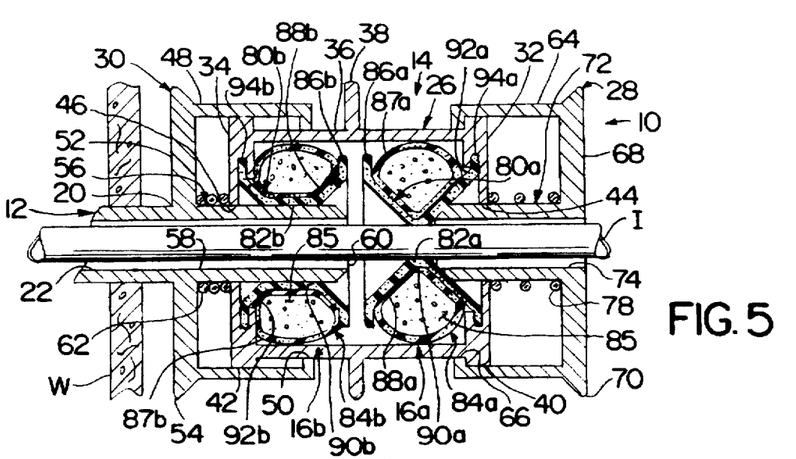
FIG. 5 is a sectional side view of the endoscopic portal of FIG. 1 showing the first, proximal universal in a sealing position and a second, distal universal seal in an open position.
Figure 6:
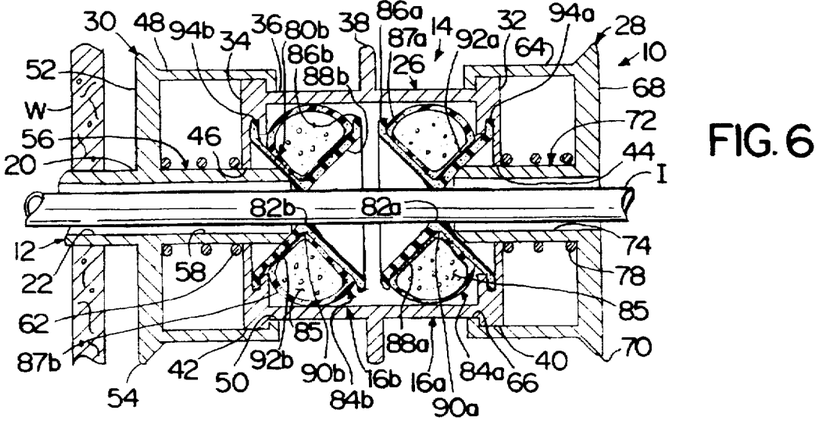
FIG. 6 is a sectional side view of the endoscopic portal of FIG. 1 showing proximal and distal universal seals in sealing positions.

With proximal seal 16a in the closed, sealing position to prevent leakage through the endoscopic portal, distal seal 16b can be opened to allow the instrument I to be moved further distally without coming into contact with the seal. Distal seal 16b is opened by moving endcap 30 longitudinally, proximally relative to main body 26 against the bias of spring 62, for example by positioning one or more fingers on the proximal side of forward wall 52 and a thumb on the proximal side of finger rest 38 and then squeezing or compressing the housing to move the endcap proximally relative to the finger rest. Endcap 30 will then be in a compressed state or condition as shown in FIG. 5, and expander 56 will be moved longitudinally, proximally into variable size passage 82b. Expander 56 overcomes the closing force or bias of seal member 80b and the compressive force of compressible member 84b to cause the seal member to be moved from the closed position wherein the variable size passage has a first cross-sectional size to an open position wherein the variable size passage has a second cross-sectional size larger than the first cross-sectional size. Once the distal end of expander 56 has entered rearward section 88b of seal member 80b the seal member will be in a fully opened position as shown in FIG. 5. Movement of seal member 80b to the open position compresses compressible member 84b which exerts an increased compressive force against the seal member since the compressible member is confined by the seal member in the housing. Since the distal seal 16b is opened by a blunt expander, tearing, puncturing and other damage to components of the seal is avoided. The lumen of expander 56 provides a passage through the seal member such that the instrument I can be moved further distally without coming into contact with the seal and without resistance to insertion which would otherwise be presented by the seal. Instrument I is advanced distally through the lumen of expander 56 into the lumen of tubular member 12 such that the instrument extends through seal 16b. Endcap 30 is then released allowing the endcap to automatically return to the non-compressed state with expander 56 being withdrawn distally from variable size passage 82b. Once the endcap has returned to the non-compressed state, distal universal seal 16b will be in a sealing position with seal member 80b urged toward the closed position by spine 99b (not shown) as well as by compressible member 84b exerting a compressive sealing force or pressure on the seal member as shown in FIG. 6. The compressible member occupies or fills the gaps or spaces between legs of the distal seal and the seal only contacts the outer surface of instrument I between the legs to complete the seal entirely along the circumference of periphery of the instrument. At this point, both of the universal seals engage the instrument I to form multiple seals therewith while allowing the instrument I to be moved longitudinally through the endoscopic portal.

Instrument I is withdrawn from endoscopic portal 10 by squeezing the housing to cause expander 56 to enter variable size passage 82b so as to be disposed between the instrument and seal member 80b. The instrument is then withdrawn through expander 56 into the axial space between seals 16a and 16b, after which the housing is released to allow distal seal 16b to automatically return to the closed or initial position. Endcap 28 is then squeezed to cause expander 72 to enter variable size passage 82a of the proximal seal so that the instrument can be withdrawn through the expander without contacting universal seal 16a. Once the instrument I is withdrawn and the endcap 28 released, proximal universal seal 16a will automatically return to the closed or initial position. It should be appreciated that since the instrument I is slidably disposed in the variable size passage, the instrument can be withdrawn from the seal without enlarging the variable size passage utilizing the expander. However, withdrawal of instrument I through the lumen of the expander has the advantage of eliminating contact by the instrument with the seal as well as eliminating resistance to withdrawal.

Figure 7:
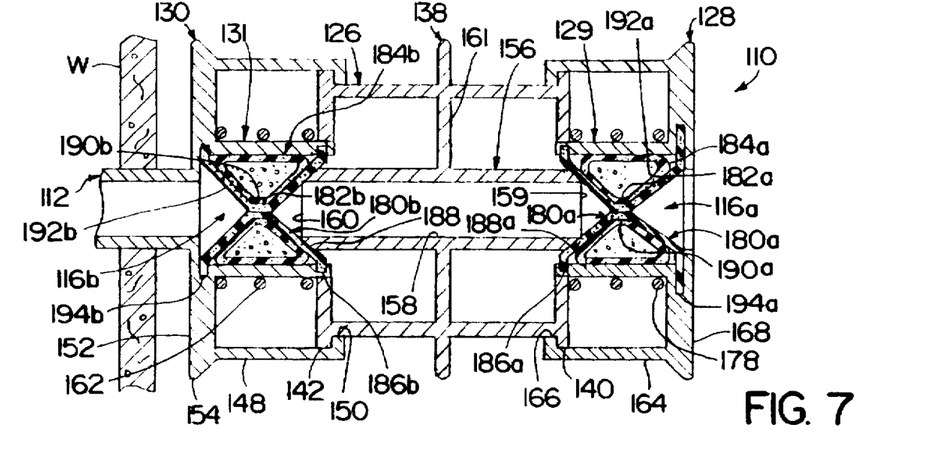
FIG. 7 is a sectional side view of a modification of the endoscopic portal according to the present invention with proximal and distal universal seals in closed positions.

Another embodiment of an endoscopic portal according to the present invention is illustrated at 110 in FIG. 7. Endoscopic portal 110 is similar to endoscopic portal 10 except that proximal and distal universal seals 116a and 116b of the modified endoscopic portal are mounted by endcaps 128 and 130, respectively; and, instead of two, separate expanders, a single expander 156 is disposed centrally between the seals in main body 126. Endcap 128 includes a cylindrical extension 129 extending distally from rearward wall 168 to receive proximal universal seal 116a. Rearward flange 194a of seal member 180a is fixedly mounted in a recess formed in the rearward wall while forward flange 186a is fixedly mounted in a recess formed at or near the distal end of the cylindrical extension. Compression member 184a is disposed around seal member 180a in the annular space between the seal member and the cylindrical extension.

Endcap 130 includes a cylindrical extension 131 extending proximally from forward wall 152 to receive distal universal seal 116b. Forward flange 194b of seal member 180b is fixedly mounted in a recess formed in forward wall 152 while rearward flange 186b is fixedly mounted in a recess formed at or near the proximal end of the cylindrical extension. Compression member 184b is disposed around seal member 180b in the annular space between the seal member and the cylindrical extension.

Expander 156 has a lumen 158 aligned with variable size passages 182a and 182b of seals 116a and 116b and the lumen of tubular member 112. The expander includes proximal and distal ends 159 and 160 each having a beveled or angled peripheral edge providing a blunt configuration. An inner wall 161 of ring-like configuration extends perpendicularly or radially relative to a longitudinal axis of the main body from the outer cylindrical surface of the expander to an inner surface of the main body to rigidly and fixedly mount the expander within the main body of the endoscopic portal.

Use of endoscopic portal 110 is similar to that described above in that endcap 128 is compressed against the bias of a spring 178 to open universal seal 116a, and endcap 130 is compressed against the bias of a spring 162 to open universal seal 116b. However, compression of endcap 128 causes forward section 188a of seal member 180a to move distally relative to proximal end 159 of the expander to position the proximal end of the expander in variable size passage 182a to open the seal. Similarly, compression of endcap 130 causes rearward section 188b of seal member 180b to move proximally against distal end 160 of the expander so that the expander will be disposed in variable size passage 182b to open the seal.

Figure 8:
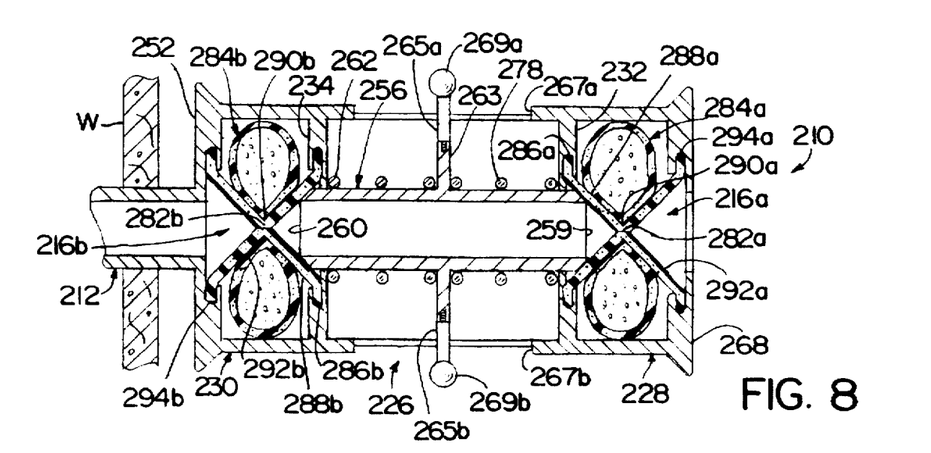
FIG. 8 is a sectional side view of another modification of the endoscopic portal according to the present invention with proximal and distal universal seals in closed positions.
Figure 9:
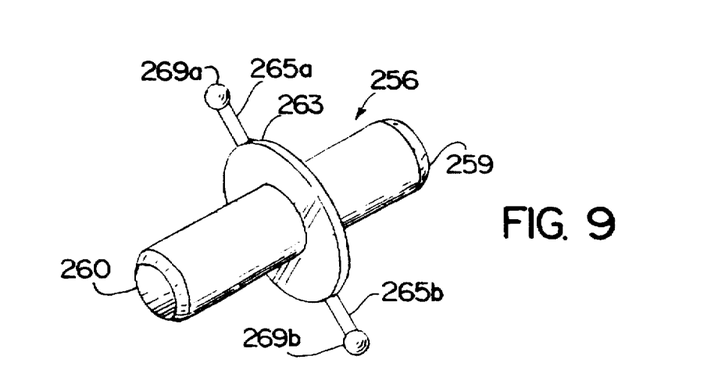
FIG. 9 is an enlarged perspective view of an expander for use with the endoscopic portal of FIG. 1.

Another embodiment of an endoscopic portal is illustrated in FIG. 8 at 210. Endoscopic portal 210 is similar to endoscopic portal 110 except that endcaps 228 and 230 are integrally formed with main body 226 and expander 256 is slidingly movable along a longitudinal axis of the main body 226. Proximal and distal universal seals 216a and 216b are disposed within proximal and distal endcap portions 228 and 230 of the housing in fixed relation to a central, main body portion 226. As best seen in FIG. 9, expander 256 carries or is formed with an outwardly protruding, radial flange 263 with post 265a and 265b extending radially outwardly of the flange through slotted openings 267a and 267b formed in the cylindrical side wall of the main body portion 126 parallel to a longitudinal axis of the housing. Posts 265a and 265b terminate externally of the housing at knobs 269a and 269b. A spring 278 or other type of bias member is disposed between flange 263 and inner wall 232 and held in compression to bias the flange in a distal direction. A second spring 262 or other bias member is disposed between flange 263 and inner wall 234 at the distal end of the housing and held in compression to exert an equal and opposite proximal bias to flange 263. As a result, expander 256 is normally held in a central, rest position between universal seals 116a and 116b with opposite axial ends 259 and 260 extending through openings in inner walls 232 and 234 to be disposed immediately adjacent the variable size passages of the seals.

Use of endoscopic portal 210 is similar to that described above with the exception that movement of expander 256 against the seals 216a and 216b is controlled by moving knobs 269a and 269b in an appropriate direction. For example, if it is desired that proximal seal 216a be opened, knobs 269a and 269b are moved proximally relative to the housing in order to force proximal end 259 of the expander into the variable size passage 282a of seal 216a. When an instrument has been passed through the proximal seal, handles 269a and 269b are released, causing the expander to move to the rest position shown in FIG. 8 and allowing seal 216a to close against the instrument in sealing relation. Handles 269a and 269b can then be moved in a distal direction relative to the housing to force distal end 260 of the expander into the variable size passage 282b of seal 216b so that the instrument can be advanced distally into the lumen of tubular member 212 after which the handles are released to allow expander 256 to move to the central, rest position and seal 216b to close against the instrument in sealing relation.

With the endoscopic portals according to the present invention, a pair of universal seals are opened with the use of one or more blunt expanders allowing instruments to be inserted through each seal via the expander without contacting the seals and without leakage through the endoscopic portal. Accordingly, the universal seals can be made of resilient, elastic materials while avoiding the risk of tearing or puncturing the elastic materials of the seal when instruments are passed therethrough. The universal seals can be designed with or without a compressible member and include a seal member normally disposed in a closed position wherein a variable size passage of the seal member has a first cross-sectional size. Where the variable size passage is completely closed in the closed position, the universal seal can serve as a valve in place of conventional trocar or portal valves. The endoscopic portals can include various valves, such as conventional flapper, ball and trumpet valves, as well as the distal end valve disclosed in applicant's prior application Ser. No. 08/383,520 filed Feb. 3, 1995 and incorporated herein by reference, for preventing fluid flow through the endoscopic portals when the seals are opened. The upstream seal is preferably not opened until after the downstream seal is in the sealing position such that fluid flow through the endoscopic portal is prevented when only one of the seals is opened. Where the endoscopic portals include both valves and universal seals, both the valves and seals can be arranged in the housing. Alternatively, the valves can be disposed in the housing and the seals can be part of an add-on component attachable to the housing. The seal members can be normally disposed in the closed position due to the configuration and/or materials of the seal members or with the use of a spine or stiffener. The seal members can have slits defining resilient legs or pivotal or bendable members, or the seal members can be essentially continuous solid structures. Where the seal members are provided with spreadable legs, the universal seals can include a compressible member disposed around the seal members or a stretchable inner layer along an inner surface of the seal members to sealingly contact an instrument along the spaces between the legs. The seal members can comprise multiple layers or seal members; and, where the multiple seal members are each slit, the slits of the seal members can be non-aligned such that the slits of the inner seal member are covered by solid portions of the outer seal member with the slits of the outer seal member being disposed over solid portions of the inner seal member. The seal members can include various bias devices such as a spine disposed on or within the material of the seal members or a stretchable ring disposed around the seal members, and the compressible members can function as a bias device to bias the seal members to the closed position. The seal members can have various configurations including various configurations providing gradual opening of the variable size passages by the distal end of the expander. It should be appreciated that the seal members can be biased toward the open position and maintained in the closed position by the expanders and/or the compressible members. The endoscopic portals according to the present invention can be designed with the seal member attached to the end cap and movable to the open position in response to movement of the seal member into the main body of the housing via squeezing operation of the housing. Depending upon the configuration of the seal member, a seal can be formed with an introduced instrument along the entire or most of the entire length of the seal member or the entire or most of the entire length of the variable size passage, or at discrete locations along the length of the seal member or the variable size passage. The compressible members can serve as the seal members for the endoscopic portals. The universal seals can extend through a cavity wall to provide a passage communicating with the cavity and for receiving instruments such that the seals serve as a portal sleeve. The expanders can have various distal end configurations to cooperate with the configurations of the seal members to facilitate opening of the variable size passages. The expanders can be utilized with any elastic universal seal, in addition to those shown herein, to open such seal to receive an instrument. With the universal seals of the present invention, instruments inserted therethrough are movable longitudinally through the seal members while a seal is maintained with the instruments. The universal seals can be provided in the main body of the housing, in the end cap or partly within the main body and partly within the end cap. Depending on the size of instruments to be inserted in the seal members, the instruments can be inserted with the seal members partially open or with the seal members fully open. The compressible members can be designed in many various ways to apply a compressive or sealing force against the seal members to form a seal with an inserted instrument. Where the compressible members include a body of compressible material disposed around the seal members, the compressible members can occupy or fill any gaps or spaces created when the seal members are moved to the open position and to contact the inserted instruments to complete the seal therewith. The endoscopic portals according to the present invention can be partially or entirely reusable or disposable for single patient use.

Movement of an expander relative to a seal can be accomplished by holding the seal in a fixed, stationary position and moving the expander, by holding the expander in a fixed, stationary position and moving the seal, or by moving both the expander and the seal.

The features of the various embodiments described above can be combined in any manner desired dependent upon the operational requirements of the procedure to be performed and the complexity of the particular design.

Inasmuch as the present invention is subject to many modifications, variations and changes in detail, it is intended that all subject matter discussed above or shown in the drawings be interpreted as illustrative only and not to be taken in a limiting sense.

What is claimed is:

1. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a tubular expander aligned with said variable size passages and having proximal and distal ends, said tubular expander being insertable in at least one of said seals to move said at least one seal from said closed position to said open position such that instruments of various sizes can be introduced through said tubular expander and said at least one seal, said tubular expander being withdrawable from said at least one seal such that said at least one seal is biased toward said closed position to contact instruments of various sizes in said variable size passage of said at least one seal to form a seal therewith; and a housing mounting said first and second seals and said tubular expander with said Proximal and distal ends of said tubular expander disposed in said housing.

2. An endoscopic portal as recited in claim 1 wherein said tubular expander is disposed between said first seal and said second seal.

3. An endoscopic portal as recited in claim 1 wherein said tubular expander is movable relative to said housing to be insertable in at least one of said seals.

4. An endoscopic portal as recited in claim 3 wherein said tubular expander is movable proximally relative to said housing to cause said proximal end to be inserted into said first seal and distally relative to said housing to cause said distal end to be inserted into said second seal.

5. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a tubular expander disposed between said first seal and said second seal in alignment with said variable size passages and including proximal and distal ends;

a housing mounting said first and second seals and said tubular expander, said tubular expander being movable relative to said housing to be insertable in said seals to move said seals from said closed position to said open position such that instruments of various sizes can be introduced through said tubular expander and said seals, said tubular expander being withdrawable from said seals such that said seals are biased toward said closed positions to contact instruments of various sizes in said variable size passages to form a seal therewith; and a bias member biasing said tubular expander toward a rest position between said first and second seals where said proximal and distal ends of said tubular expander are axially spaced from respective variable size passages of said first and second seals so that said seals will normally be in said respective closed positions said tubular expander being movable proximally relative to said housing to cause said proximal end to be inserted into said first seal and distally relative to said housing to cause said distal end to be inserted into said second seal.

6. An endoscopic portal as recited in claim 2 wherein at least one of said seals is longitudinally movable relative to said housing to insert said tubular expander therein in a manner to move said at least one seal from said closed position to said open position such that instruments of various sizes can be introduced through said tubular expander and said at least one seal.

7. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a tubular expander disposed between said first seal and said second seal in alignment with said variable size passages and including proximal and distal ends, said tubular expander being insertable in at least one of said seals to move said at least one seal from said closed position to said open position such that instruments of various sizes can be introduced through said tubular expander and said at least one seal, said tubular expander being withdrawable from said at least one seal such that said at least one seal is biased toward said closed position to contact instruments of various sizes in said variable size passage of said at least one seal to form a seal therewith;

a housing mounting said first and second seals and said tubular expander, at least one of said seals being movable relative to said housing to receive said tubular expander in a manner to move said at least one seal from said closed position to said open position such that instruments of various sizes can be introduced through said tubular expander and said at least one seal, said first seal being movable distally relative to said tubular expander to cause said proximal end of said tubular expander to be inserted therethrough, and said second seal being movable proximally relative to said tubular expander to cause said distal end of said tubular expander to be inserted therethrough.

8. An endoscopic portal as recited in claim 7 and further comprising bias means for biasing said seals away from said tubular expander so that said seals will normally be in said respective closed positions.

9. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distaly of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a first tubular expander disposed proximally of said first seal in alignment with said variable size passage of said first seal and being insertable in said first seal to move said first seal from said closed position to said open position such that instruments of various sizes can be introduced through said first tubular expander and said first seal, said first tubular expander being withdrawable from said first seal such that said first seal is biased toward said closed position to contact instruments of various sizes in said variable size passage of said first seal to form a seal therewith; and a second tubular expander disposed distally of said second seal in alignment with said variable size passage of said second seal, said second tubular expander being insertable in said second seal to move said second seal from said closed position to said open position such that instruments of various sizes can be introduced through said second tubular expander and said second seal, said second tubular expander being withdrawable from said second seal such that said second seal is biased toward said closed position to contact instruments of various sizes in said variable size passage of said second seal to form a seal therewith.

10. An endoscopic portal as recited in claim 9 and further comprising a housing mounting said first and second seals and said first and second tubular expanders.

11. An endoscopic portal as recited in claim 10 wherein said first tubular expander is movable relative to said housing to be insertable in said first seal and said second tubular expander is movable relative to said housing to be insertable in said second seal.

12. An endoscopic portal as recited in claim 11 and further comprising bias means for biasing said first and second tubular expanders away from said first and second seals, respectively, so that said seals will normally be in said respective closed positions.

13. An endoscopic portal as recited in claim 12 wherein said housing includes first and second endcaps slidably mounted at opposite axial ends of said housing, and wherein said first tubular expander is mounted in said first endcap and said second tubular expander is mounted in said second endcap.

14. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being dispose d in a closed position wherein said variable size passage of said second seal is closed and being movable to an open position wherein said variable size passage of said second seal is open;

a tubular expander disposed between said first seal and said second seal in alignment with said variable size passages and being insertable in at least one of said seals to move said at least one seal from said closed position to said open position such that instruments of various sizes can be introduced through said tubular expander and said at least one seal, said tubular expander being withdrawable from said at least one seal such that said at least one seal is biased toward said closed position to contact instruments of various sizes in said variable size passage of said at least one seal to form a seal therewith; and a housing mounting said first and second seals and said tubular expander, at least one of said seals being movable relative to said housing to receive said tubular expander therein in a manner to move said at least one seal from said closed position to said open position such that instruments of various sizes can be introduced through said tubular expander and said at least one seal, said housing including first and second endcaps slidably mounted at axially opposed ends of said housing, said first seal being mounted in said first endcap and said second seal mounted in said second endcap and said tubular expander being fixedly mounted in said housing between said endcaps.

15. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a tubular expander disposed between said first seal and said second seal in alignment with said variable size passages and being insertable in at least one of said seals to move said at least one seal from said closed position to said open position such that instruments of various sizes can be introduced through said tubular expander and said at least one seal, said tubular expander being withdrawable from said at least one seal such that said at least one seal is biased toward said closed position to contact instruments of various sizes in said variable size passage of said at least one seal to form a seal therewith;

a housing mounting said first and second seals and said tubular expander, said tubular expander being movable relative to said housing to be insertable in at least one of said seals; and a handle extending through a slot in said housing to couple with said tubular expander.

16. A method of introducing an instrument in a body cavity using a sleeve having a distal end, a proximal end and a lumen between the distal and proximal ends, a first seal having a variable size passage, a second seal disposed distally of the first seal and having a variable size passage axially aligned with the variable size passage of the first seal, and a tubular expander longitudinally aligned with the variable size passages and being insertable in at least one of the seals, said method comprising the steps of introducing the distal end of the sleeve in a body cavity;

moving the tubular expander into the variable size passage of the first seal to enlarge the variable size passage to receive an instrument;

introducing the instrument through the tubular expander such that the instrument extends through the first seal;

withdrawing the tubular expander from the variable size passage of the first seal to allow the first seal to resiliently engage the instrument and form a seal therewith;

moving the tubular expander into the variable size passage of the second seal to enlarge the variable size passage to receive the instrument;

advancing the instrument distally through the tubular expander such that the instrument extends through the second seal; and withdrawing the tubular expander from the variable size passage of the second seal such that the second seal resiliently engages the instrument and forms a seal therewith.

17. A method of introducing an instrument in a body cavity as recited in claim 16 wherein said step of moving the tubular expander into the variable size passage of the first seal includes moving a first tubular expander relative to the first seal and wherein said step of moving the tubular expander into the variable size passage of the second seal includes moving a second tubular expander relative to the second seal.

18. A method of introducing an instrument in a body cavity as recited in claim 16 wherein said step of moving the tubular expander into the variable size passage of the first seal includes moving the tubular expander proximally from a rest position disposed between the first and second seals and said step of moving the tubular expander into the variable size passage of the second seal includes moving the tubular expander distally relative to the second seal from the rest position.

19. A method of introducing an instrument in a body cavity as recited in claim 18 wherein said step of moving the tubular expander proximally relative to the first seal includes holding the tubular expander stationary within a housing and moving the first seal distally relative to the housing and wherein said step of moving the tubular expander distally relative to the second seal includes holding the tubular expander substantially stationary relative to a housing and moving the second seal proximally relative to the housing.

20. An endoscopic portal for establishing communication with a body cavity for the introduction of instruments through the endoscopic portal comprising a first seal having a variable size passage to permit instruments of varying sizes to be passed therethrough, said first seal being disposed in a closed position wherein said variable size passage is closed and being movable to an open position wherein said variable size passage is open;

a second seal disposed distally of said first seal and having a variable size passage axially aligned with said variable size passage of said first seal to permit instruments of varying sizes to be passed therethrough, said second seal being disposed in a closed position wherein said variable size passage of said second seal is closed and being movable to an open position wherein said variable size passage of said second seal is open;

a tubular expander aligned with said variable size passages and being insertable in at least one of said seals to move said at least one seal from said closed position to said open position such that instruments of various sizes can be introduced through said tubular expander and said at least one seal, said tubular expander being withdrawable from said at least one seal such that said at least one seal is biased toward said closed position to contact instruments of various sizes in said variable size passage of said at least one seal to form a seal therewith;

a housing mounting said first and second seals and said tubular expander; and a bias member disposed in said housing and maintaining said tubular expander in a position of withdrawal from said at least one seal such that said at least one seal is biased toward said closed position, said bias member permitting movement of said tubular expander to a position of insertion in said at least one seal such that said at least one seal is moved to said open position.

* * * * *